United States Patent [19]
Baker

[11] Patent Number: 5,643,238
[45] Date of Patent: Jul. 1, 1997

[54] ABSORBENT CORE STRUCTURE COMPRISED OF STORAGE AND ACQUISITION CELLS

[75] Inventor: Andrew T. Baker, Lawrenceville, Ga.

[73] Assignee: Paragon Trade Brands, Inc., Norcross, Ga.

[21] Appl. No.: 537,244

[22] Filed: Sep. 29, 1995

[51] Int. Cl.$^6$ .......................... A61F 13/15; B32B 31/00; B32B 7/12
[52] U.S. Cl. .......................... 604/368; 604/369; 604/378; 604/385.1; 156/276; 156/291
[58] Field of Search .......................... 604/367, 368, 604/369, 374, 378, 379, 380, 382, 383, 385.1; 156/276, 292, 308.4, 291

[56] References Cited

U.S. PATENT DOCUMENTS

| | | | |
|---|---|---|---|
| Re. 32,957 | 6/1989 | Elias . | |
| 3,908,659 | 9/1975 | Wehrmeyer et al. | 604/380 |
| 4,055,180 | 10/1977 | Karami | 604/368 |
| 4,235,237 | 11/1980 | Mesek et al. . | |
| 4,260,443 | 4/1981 | Lindsay et al. | 604/368 |
| 4,333,462 | 6/1982 | Holtman et al. . | |
| 4,333,463 | 6/1982 | Holtman . | |
| 4,360,021 | 11/1982 | Stima | 604/369 |
| 4,560,372 | 12/1985 | Pieniak . | |
| 4,578,068 | 3/1986 | Kramer et al. . | |
| 4,834,735 | 5/1989 | Alemany et al. . | |
| 4,935,022 | 6/1990 | Lash et al. . | |
| 4,960,477 | 10/1990 | Mesek . | |
| 4,988,344 | 1/1991 | Reising et al. . | |
| 4,988,345 | 1/1991 | Reising . | |
| 4,994,053 | 2/1991 | Lang | 604/367 |
| 5,021,050 | 6/1991 | Iskra . | |
| 5,047,023 | 9/1991 | Berg . | |
| 5,061,259 | 10/1991 | Goldman et al. . | |
| 5,098,423 | 3/1992 | Pieniak et al. . | |
| 5,141,794 | 8/1992 | Arroyo . | |
| 5,147,343 | 9/1992 | Kellenberger . | |
| 5,149,335 | 9/1992 | Kellenberger et al. . | |
| 5,156,902 | 10/1992 | Pieper et al. . | |
| 5,173,351 | 12/1992 | Ruppel et al. | 604/380 |
| 5,248,524 | 9/1993 | Soderlund . | |
| 5,260,345 | 11/1993 | DesMarais et al. . | |
| 5,281,207 | 1/1994 | Chmielewski et al. . | |
| 5,314,738 | 5/1994 | Ichikawa . | |
| 5,354,290 | 10/1994 | Gross . | |
| 5,356,403 | 10/1994 | Faulks et al. . | |
| 5,364,686 | 11/1994 | Disselbeck et al. . | |
| 5,411,497 | 5/1995 | Tanzer et al. . | |

FOREIGN PATENT DOCUMENTS 7700037  9/1978  France .

*Primary Examiner*—Robert A. Clarke
*Assistant Examiner*—Ki Yong O
*Attorney, Agent, or Firm*—Klarquist Sparkman Campbell Leigh & Whinston, LLP

[57] ABSTRACT

The present invention provides an absorbent core structure comprising storage cells and acquisition cells in a honeycomb-like configuration. Absorbent core structures according to the invention are useful, for example, for absorbent cores for disposable absorbent garments. Within the storage cells of the absorbent core structure is deposited a quantity of a superabsorbent material. The acquisition cells are devoid of superabsorbent material or other materials that would impede liquid movement therethrough and are preferably open. The acquisition cells can thus function as channels that allow liquids to be freely distributed within the absorbent core structure by mass flow and/or capillary action, thus helping to prevent gel blocking.

18 Claims, 3 Drawing Sheets

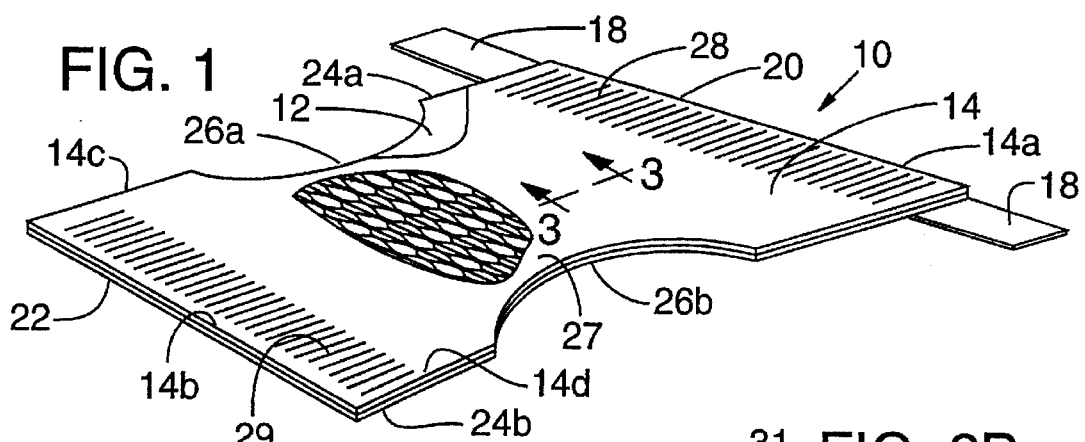
FIG. 1
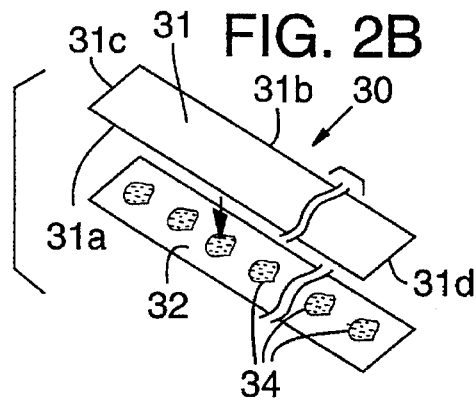
FIG. 2B
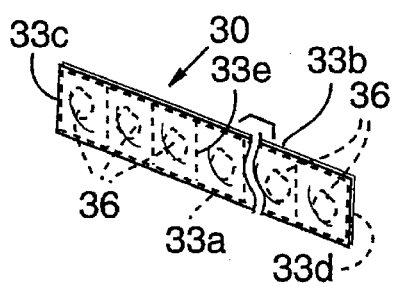
FIG. 2A
FIG. 2C
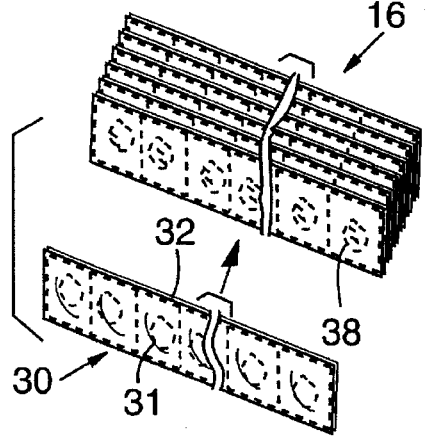
FIG. 2D
FIG. 2E
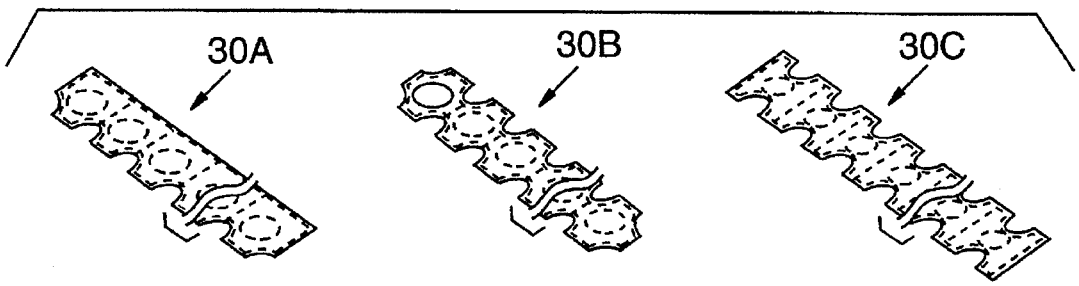

ABSORBENT CORE STRUCTURE COMPRISED OF STORAGE AND ACQUISITION CELLS

FIELD OF THE INVENTION

The present invention relates generally to absorbent core structures for a disposable absorbent garment and, more particularly, to absorbent core structures comprising storage cells containing a superabsorbent material and acquisition cells devoid of materials that would impede liquid movement therethrough.

BACKGROUND OF THE INVENTION

Traditionally, disposable absorbent garments such as infant diapers or training pants and adult incontinence briefs are constructed with a moisture-impervious outer, or backing, sheet, a moisture-pervious body-contacting inner, or liner, sheet, and a moisture-absorbent core sandwiched and encased between the liner and backing sheets.

Much effort has been expended to find cost-effective materials for absorbent cores that display good liquid absorbency and retention. Superabsorbent materials in the form of granules, beads, fibers, etc., have been favored for such purposes. Such superabsorbent materials are generally polymeric gelling materials that are capable of absorbing large quantities of liquids such as water and body wastes relative to their weight and of retaining such absorbed materials even under moderate pressure.

The ability of a superabsorbent material to absorb liquid is dependent upon the form, position, and/or manner in which particles of the superabsorbent are incorporated into the absorbent core. Whenever a particle of the superabsorbent material in an absorbent core is wetted, it swells and forms a gel. Gel formation can block liquid transmission into the interior of the absorbent core, a phenomenon called "gel blocking." Gel blocking in and adjacent a zone in an absorbent core of initial liquid contact prevents liquid from rapidly diffusing or wicking past the "blocking" particles of superabsorbent into the rest of the absorbent core; further imbibition of liquid by the absorbent core must then take place via a diffusion process that can be much slower than the rate at which liquid is applied to the core. Gel blocking can thus result in leakage from the absorbent article well before the absorbent core is fully saturated.

Efficient imbibition of liquid by the absorbent core at the point of initial liquid contact and rapid distribution of the liquid away from this point is necessary to insure that the absorbent core has sufficient capacity to absorb subsequently deposited liquids. What is needed is an absorbent core that quickly imbibes and distributes large quantities of liquids throughout the core while minimizing gel blocking during initial liquid contact.

Preferably, the absorbent core is also thin in order to improve the appearance of a garment with such an absorbent core and the comfort of the wearer of the garment. The importance of thin, comfortable garments is disclosed, for example, in U.S. Pat. No. 5,098,423 (Pieniak et al.), which is incorporated herein by reference.

SUMMARY OF THE INVENTION

One object of the present invention is to provide a thin, highly absorbent core structure useful, for example, for disposable absorbent garments. To that end, the present invention provides absorbent core structures comprising a plurality of discrete "storage cells," within each of which is disposed a quantity of an absorbent and/or superabsorbent material, and a plurality of "acquisition cells" that are devoid of material that would impede the movement of liquid therethrough and that are preferably empty. The acquisition cells function as channels to distribute liquids throughout the absorbent-core structure, thereby overcoming the problem of gel blocking and promoting rapid liquid transfer throughout the absorbent core structure.

In order to produce a layer of the absorbent core structure according to one embodiment of the invention, discrete quantities of an absorbent and/or superabsorbent material are deposited at spaced locations between liquid-pervious strips or sheets (or between facing halves of a pleated or folded double-width strip or sheet or by any other arrangement that provides at least two facing surfaces wherein absorbent or superabsorbent material can be contained therebetween). The sheets are then bonded or attached to each other along open edges and at spaced locations between the deposited superabsorbent material by any conventional adhesive or bonding means, e.g., sonic bonding. Each absorbent layer, or array, so produced comprises a plurality of discrete storage cells, in each of which is captured a quantity of the superabsorbent material.

In order to produce an absorbent core structure according to one embodiment of the invention, absorbent arrays are disposed contiguously with respect to each other. Preferably, the absorbent arrays are all the same size and their edges are aligned with each other. A liquid-permeable sheet may optionally be interposed between adjacent absorbent arrays.

Adjacent absorbent arrays can be attached to each other by any conventional adhesive or bonding means, e.g., by adhesive applied to one (or both) exterior surface(s) of each absorbent array (except, perhaps, the outermost surfaces of the absorbent core structure), e.g., at spaced apart locations approximately at the mid-region of each of the storage cells in the arrays.

Acquisition cells are formed between and bounded by adjacent absorbent arrays. Additional acquisition cells or spaces or openings may also be provided elsewhere in the absorbent core structure, e.g., in the absorbent arrays thereof, in order to facilitate liquid transfer throughout the absorbent core structure.

Another object of the present invention is to provide a wide variety of disposable absorbent garments incorporating an absorbent core structure according to the invention. In one embodiment of the invention, such a garment is provided, the garment comprising a moisture-impervious backing sheet and a moisture-pervious liner sheet between which is an absorbent core structure according to the present invention. When superabsorbent material in the storage cells absorbs liquid, the resulting swelling of the superabsorbent material causes the storage cells to swell. The swelling of the storage cells increases the volume of acquisition cells between adjacent absorbent arrays.

These and other objects, features and advantages of the present invention will become apparent to those skilled in the art from the following description and drawings.

BRIEF DESCRIPTION OF THE DRAWINGS

FIG. 1 is an isometric view of an absorbent garment incorporating an absorbent core according to the present invention, with portions of a liner sheet broken away to show the absorbent core.

FIGS. 2A-E are schematic views showing a method of manufacturing an absorbent array and an absorbent core structure according to an embodiment of the invention. A-C:

A method of manufacturing a single absorbent array. D: A method of manufacturing an absorbent core structure from multiple absorbent arrays. E: Three examples of an absorbent array in which one (30A) or both longitudinal edges (30B, 30C) is scalloped.

Figure 3:
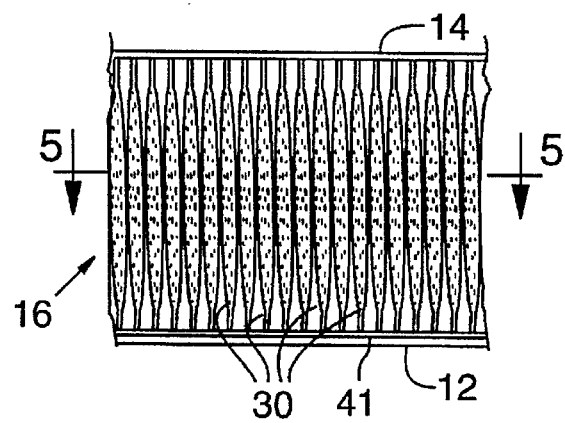

FIG. 3 is an enlarged cross-sectional view of a portion of the absorbent garment shown in FIG. 1 taken along line 3—3.

Figure 4:
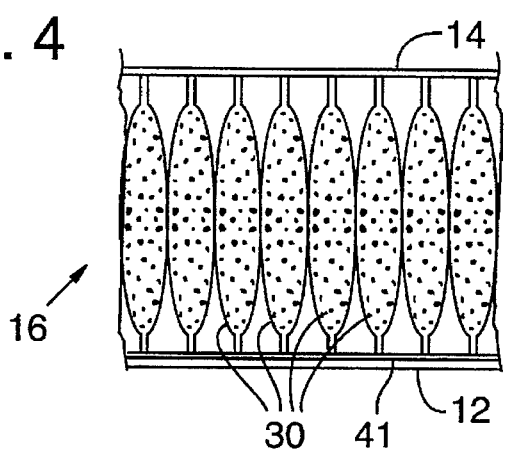

FIG. 4 is a cross-sectional view of the absorbent garment shown in FIG. 3 after absorbing liquid.

Figure 5:
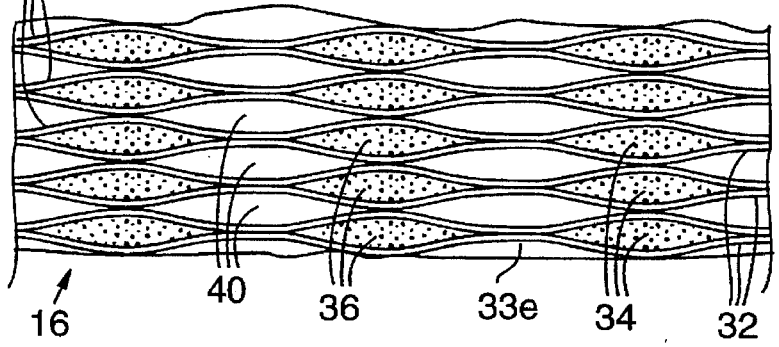

FIG. 5 is an enlarged cross-sectional view of the absorbent garment shown in FIG. 3 taken along a line 5—5.

Figure 6:
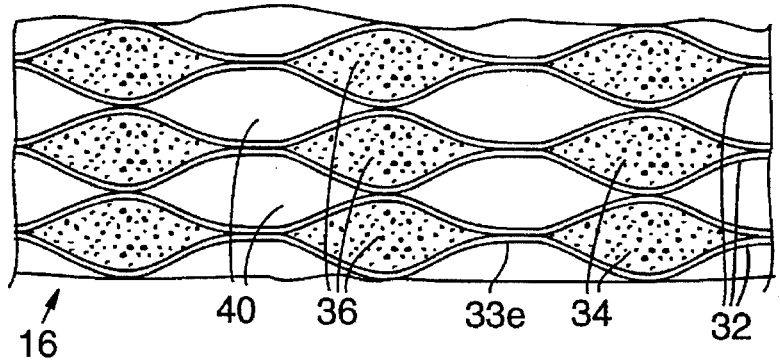

FIG. 6 is a cross-sectional view of the absorbent garment as shown in FIG. 5 after absorbing liquid.

Figure 7:
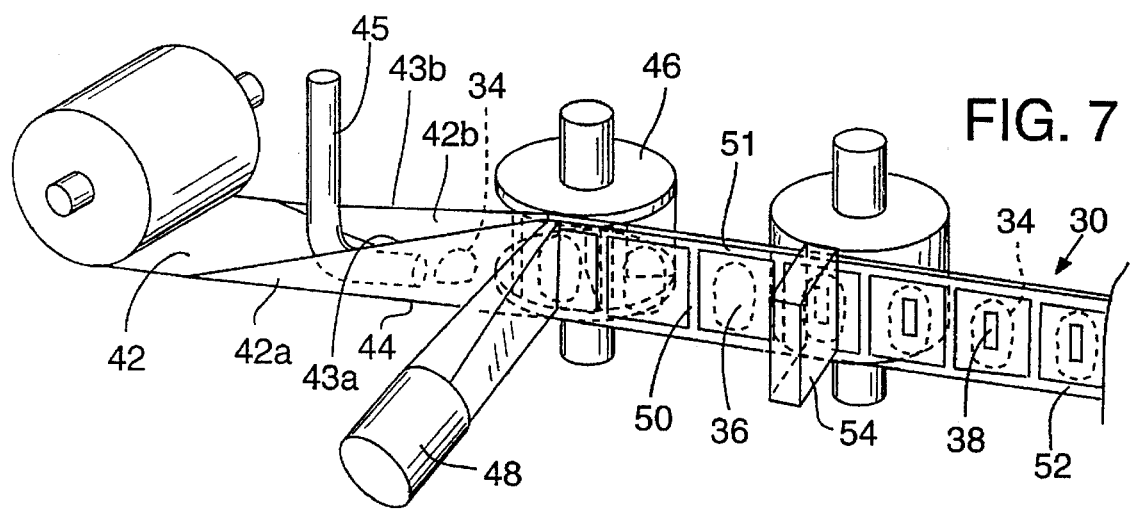

FIG. 7 is a simplified isometric view of a method for manufacturing an absorbent array of an absorbent core structure according to an embodiment of the invention.

Figure 8:
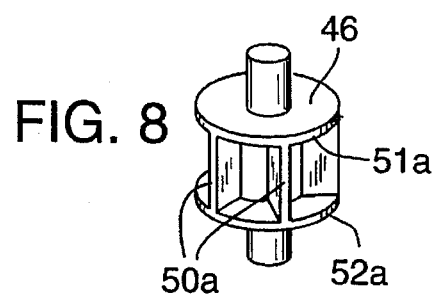

FIG. 8 is an isometric view of a mandrel used for sonic bonding sheet material to produce an absorbent array by the method shown in FIG. 7.

Figure 9:
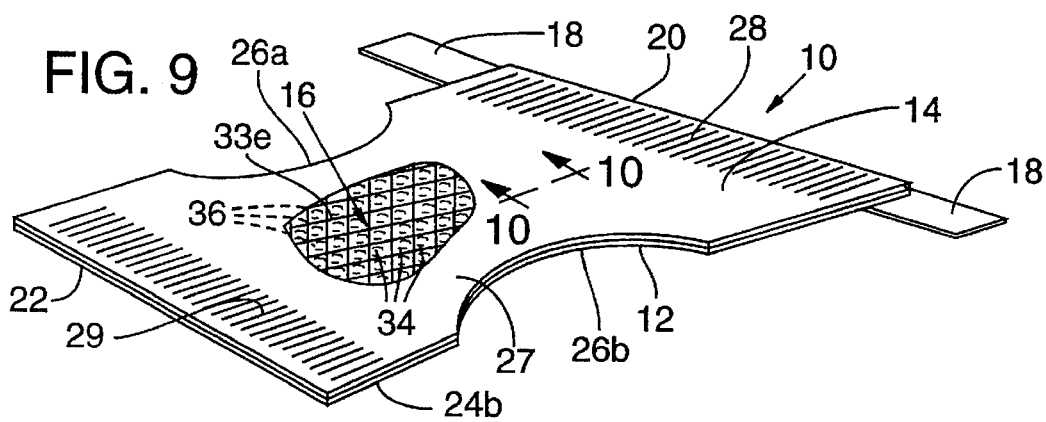

FIG. 9 is an isometric view of an absorbent garment incorporating an alternative embodiment of an absorbent core according to the present invention, with portions of the liner sheet broken away to show the absorbent core.

Figure 10:
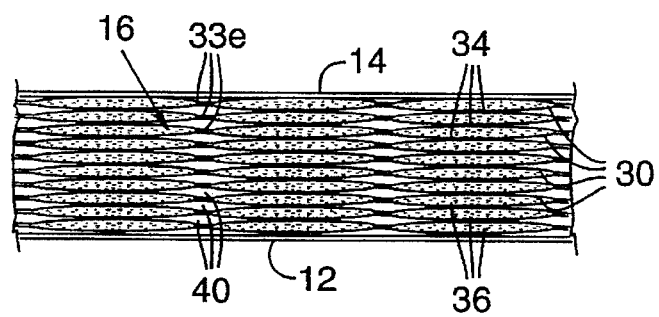

FIG. 10 is an enlarged cross-sectional view of the absorbent garment shown in FIG. 9 taken along line 10—10.

DETAILED DESCRIPTION OF PREFERRED EMBODIMENT

The present invention provides absorbent core structures having both discrete storage cells and acquisition cells, useful, for example, for incorporation into disposable absorbent garments.

FIG. 1 illustrates an embodiment of a disposable absorbent garment 10, typically for use as a baby or infant diaper or as an adult incontinence brief. The absorbent garment 10 can also be sealed or joined along the opposed side edges 24a, 24b to form a pull-on style training pant.

The garment 10 has a moisture-impervious outer (or backing) layer (or sheet) 12 and a moisture-pervious inner (liner) layer (sheet) 14. A moisture-absorbent core (or pad) 16, incorporating an absorbent core structure according to an embodiment of the invention, is disposed superposedly on at least a portion of backing sheet 12 so as to be sandwiched between the backing sheet 12 and liner sheet 14. The resulting trilaminar structure can be held together by any of various conventional means, e.g., adhesive or other bonding means (e.g., sonic bonding, embossing, needle punch, etc.).

The garment 10 has a first laterally extending waist edge 20, and a second waist edge 22. The first and second waist edges 20 and 22, respectively, are spaced so as to be situated along back and front waist regions, respectively, of a wearer of the garment. The garment 10 also has opposed first and second side edges, or margins, 24a, 24b, respectively.

The liner sheet 14 has opposed side edges 24c, 24d and first and second waist edge regions 24e, 24f that can be coextensive with the backing sheet 12 (as shown) or can terminate at some point inwardly from the edges of the backing sheet, as desired.

Such garments 10 also typically include outer leg gathers or seals, stretchable waistbands, and tapes or other fasteners at the waist. A pair of tape fasteners are indicated generally at 18 extending outwardly from opposite side edges 24a, 24b adjacent first waist edge 20, which is usually situated on the back waist region of the wearer.

The side edges 24a, 24b have incut leg regions 26a, 26b adapted to fit about the legs of a wearer. The garment thus has a generally hourglass-shaped configuration so as to define a crotch region 27 located generally between the incut leg regions 26a, 26b. The crotch region 27 has a narrower width than the waist edges 20, 22.

Waist gathers 28, 29, are preferably provided adjacent the waist edges 20, 22, respectively. The waist gathers are preferably formed by incorporation of elastic material or the like adjacent the waist edges so as to form rugosities in the waist edges. The waist gathers 28, 29 provide a more comfortable fit for the wearer.

The absorbent core, or pad, 16, comprises an absorbent core structure as described in detail below. The absorbent core 16 is generally disposed in the crotch region 27. The absorbent core 16 may have a rectangular shape or any other suitable shape such as an hourglass configuration.

Due to the wide variety of backing and liner sheet constructions and materials currently available, the invention is not intended to be limited to any specific materials or constructions of these components. The backing sheet 12 is of any suitable pliable liquid-impervious material known in the art. Typical backing sheet materials include films of polyethylene, polypropylene, polyester, nylon, and polyvinyl chloride and blends of these materials. For example, the backing sheet can be of a pigmented polyethylene film having a thickness in the range of 0.02–0.04 mm. The moisture-pervious liner sheet 14 can be of any suitable relatively liquid-pervious material known in the art that permits passage of liquid therethrough. Nonwoven liner sheet materials are exemplary because such materials readily allow the passage of liquids to the underlying absorbent core 16. Examples of suitable liner sheet materials include nonwoven webs of nylon, polyester, and polypropylene fibers and blends of these materials. Suitable commercially available liner sheet materials include Cerex® (James River Corporation), Reemay® (Intertec Corporation), and Sonterra® (Dupont Corporation). The liner sheet can comprise multiple layers. See, e.g., U.S. Pat. No. 5,188,624 (Young, Sr., et al.), incorporated herein by reference, for additional information regarding materials and manufacture of absorbent garments.

Those skilled in the art will appreciate that the absorbent garments of the present invention may incorporate a wide variety of additional elements conventionally used in absorbent garments (e.g., additional liner sheets, layers of natural or synthetic fibers, etc.) and that the elements provided herein can be altered or adapted by conventional means.

For example, a suitable liner sheet may be placed between the absorbent core and the liquid-impervious backing sheet to facilitate free liquid transport within the absorbent core. One may also place a layer of comminuted wood (fluff) pulp or a mixture of natural or synthetic fibers (preferably a thin layer) between the absorbent core and the liquid-impervious backing sheet to give the absorbent garment a softer feel and to assist in containment of free liquid. Additionally, a liner sheet or compacted fiber layer may be placed around the outer margins of the absorbent core.

Absorbent core structures according to the invention also are useful for a wide variety of other absorbent garments and related uses, including, but not limited to, adult incontinence garments, sanitary napkins, disposable panties, children's training pants, bed pads, and the like.

In general, each absorbent array 30 of the absorbent core structure 16 is produced by capturing a quantity of absorbent and/or superabsorbent material at spaced locations between at least two facing surfaces of liquid-pervious strips or sheets, wherein the facing surfaces are provided by two opposed strips or sheets, or by facing surfaces of a single pleated or folded strip or sheet, or by any other arrangement that provides at least two facing surfaces between which an absorbent and/or superabsorbent material can be captured.

FIGS. 2A–D together show a preferred method of manufacturing an absorbent array 30 and an absorbent core structure 16 according to a preferred embodiment of the invention, the absorbent core structure 16 comprising multiple absorbent arrays 30 configuration as shown.

As shown in FIG. 2B, each absorbent array 30 of the absorbent core structure 16 preferably comprises two opposed strips 31, 32 of a non-woven liquid-pervious sheet material. (The strip 32 is shown in FIG. 2A.) The strips 31, 32 preferably have identical size and shape. The strips 31, 32 each have opposed first and second longitudinal edges, or margins, 31a, 31b, and 32a, 32b, respectively, and opposed first and second end edges 31c, 31d, and 32c, 32d, respectively. On the strip 32 is deposited discrete quantities of liquid-absorbent material 34 (FIG. 2B), preferably a superabsorbent material (or, if desired, a mixture of a superabsorbent material with another material, e.g., another liquid-absorbent or fibrous material) at spaced locations. The two strips 31, 32 are bonded, sealed, or otherwise attached to each other substantially superposedly by any conventional means to create interstrip bonds along each of their combined longitudinal edges 33a, 33b and end edges 33c, 33d and between each location of superabsorbent material 33e (see FIG. 2C). As shown in FIG. 2D, the bonds thus define multiple storage cells 36 in each absorbent array 30, each cell 36 containing a quantity of the superabsorbent material 34.

The length and or width of each of the strips 31, 32 need not be the same. In fact, in some embodiments of the invention, it may be desirable to locate a shorter or narrower strip centrally along the surface of a longer or wider strip, leaving free ends 32c and/or 32d, or edges, 32a and/or 32b, or both. The free ends or edges can then be fastened to other parts of an absorbent garment incorporating the absorbent core structure, e.g., to the liner sheet 14 or the backing sheet 12.

In addition, although the first and second longitudinal edges 31a, 31b, and 32a, 32b and end edges 31c, 31d and 32c, 32d of strips 31 and 32, respectively, are shown in FIG. 2A as being straight, these edges may have any shape or conformation, e.g., scalloped, fringed or digitated, etc. For example, scalloping one or more edges, e.g., as shown in FIG. 2E, may facilitate the movement of free liquid throughout the absorbent core structure.

The storage cells 36 thus formed can be generally square or rectangular in shape (FIGS. 2C–2D), each storage cell being analogous to a ravioli having a partial "filling" of superabsorbent material. Each storage cell 36 is discrete, i.e., the contents of each storage cell are separated from the contents of all other storage cells and from the contents, if any, of acquisition cells 40 (described below), even though storage and acquisition cells are in liquid contact with each other.

Those skilled in the art will appreciate that absorbent core structures may combine absorbent arrays according to the present invention with conventional liquid-absorbent or non-absorbent material in various ways. For example, an absorbent core may comprise absorbent arrays according to the present invention alternating with layers of a conventional liquid-absorbent material such as fluff pulp. Alternatively, an absorbent core may combine regions comprising absorbent arrays according to the present invention with regions consisting of conventional materials such as conventional fluff pulp. For example, an absorbent core may comprise (1) a discrete panel comprising overlapping absorbent arrays according to the present invention positioned towards front and central areas of an absorbent garment and (2) conventional fluff pulp in the remaining areas of the absorbent core.

The liquid-pervious sheets 31, 32 from which absorbent arrays 30 are manufactured can, for example, be non-woven webs of carded polyester fibers with a latex binder, spun-bonded continuous polypropylene fibers thermally bonded together, cellulosic pulp fibers, or other appropriate materials known in the art.

The quantity of superabsorbent material 34 in each storage cell 36 preferably only partially fills each storage cell so as to allow room for swelling of the superabsorbent material upon fluid absorption without rupturing the storage cell.

The superabsorbent material 34 can be any suitable particulate (e.g., flaked, particulate, granular, or powdered) or fibrous material known in the art that has the ability to absorb large quantities of liquids, including body fluids, preferably in excess of 30 to 40 parts of liquid per part thereof. Superabsorbent materials generally fall into three classes: starch graft copolymers, cross-linked carboxymethylcellulose derivatives, and modified hydrophilic polyacrylates. Exemplary superabsorbent materials include, but are not limited to: carboxylated cellulose, hydrolyzed acrylonitrile-grafted starch, acrylic acid derivative polymers, polyacrylonitrile derivatives, polyacrylamide-type compounds, and saponified vinyl acetate/methyl acrylate copolymers. Specific examples of commercially available superabsorbent materials are "Sanwet" (supplied by Sanyo Kasei Kogyo Kabushiki Kaisha) and "Sumika Gel" (supplied by Sumitomo Kagaku Kabushiki Kaisha).

The superabsorbent material can be mixed with other materials known in the art, preferably fibrous materials, to form a liquid-absorbent matrix. These additional materials include, but are not limited to, hydrophilic fibrous materials such as cellulose fibers, modified cellulose fibers (e.g., comminuted wood pulp or internally cross-linked cellulose fibers), rayon, polyester fibers such as polyethylene terephthalate (DACRON™), hydrophilic nylon (HYDROFIL™), and hydrophilized hydrophobic fibers (e.g., surfactant- or silica-treated thermoplastic fibers derived, for example, from polyolefins).

As shown in FIG. 2D, an absorbent core structure according to an embodiment of the invention can be produced by disposing multiple absorbent arrays 30 laterally adjacent to and in contact with each other such that the end edges 33c, 33d of adjacent absorbent arrays are aligned. As shown in FIG. 3, each absorbent array 30 comprises a linear array of storage cells 36 that are oriented "vertically" in the absorbent core, i.e., substantially perpendicular to the plane of the backing sheet 12 and of the liner sheet 14, with one longitudinal edge of the array adjacent the liner sheet 14 and the other longitudinal edge adjacent the backing sheet 12. Alternatively, the absorbent arrays can be oriented "horizontally" in the absorbent core, in which case the general plane of the absorbent array is parallel to the planes of the backing sheet 12 and liner sheet 14. The arrays 30 can be attached to each other by any conventional means, e.g., adhesive or bonding means (e.g., sonic bonding, embossing, needle punch, etc.). For example, as shown in FIGS. 2D and 7, a spot (or line or stripe) of adhesive 38 is applied externally to each array to be bonded to another array at regularly spaced intervals, e.g., on each storage cell 36.

Adjacent absorbent arrays 30 are preferably attached to each other at spaced locations, preferably by adhesive means, as described above. Optionally, liquid pervious sheets can be interposed between and bonded to adjacent absorbent arrays.

FIG. 3 shows absorbent arrays 30 in the absorbent core structure 16 in a "vertical" orientation in which the absorbent core structure 16 is sandwiched between a liquid-impervious backing sheet 12 and a liquid-pervious liner sheet 14. As superabsorbent material 34 in the storage cells 36 absorbs liquid and swells, the storage cells 36 expand, as shown in FIG. 4.

FIGS. 5 and 6 show acquisition cells 40 formed between the absorbent arrays 30 of the absorbent core structure 16. When the absorbent arrays 30 are assembled together to form an absorbent core structure 16 as shown in FIG. 2D, the storage cells 36 alternate with acquisition cells 40 in a honeycomb-like configuration in the absorbent core structure 16.

The acquisition cells 40 are preferably devoid of superabsorbent material or other materials that would impede the movement of liquid therethrough and are preferably open, i.e., empty. Within such acquisition cells 40, liquid can move freely by mass flow. Liquid can also flow by capillary action, e.g., in the sheet material 31, 32 bounding each acquisition cell 40. Thus, the acquisition cells 40 function as fluid channels that allow fluids to be readily distributed throughout the absorbent core structure. The acquisition cells 40 thus help to prevent "gel blocking" and ensure that liquid is quickly carried away from the point of deposition, i.e., away from the skin of the wearer of an absorbent garment incorporating an absorbent core according to the present invention.

As shown most clearly in FIG. 6, expansion of the storage cells 36 upon liquid absorption causes the acquisition cells 40 to also expand, thereby facilitating fluid delivery throughout the absorbent core structure.

The acquisition cells 40 preferably contain no materials when dry so as to allow the absorbent core structure to be made as thin as possible. If desired, some or all of the acquisition cells can contain a liquid-absorbent or non-absorbent material known in the art that would produce minimal impedance to the movement of liquid through the acquisition cells. For example, an appropriate material can be (1) disposed between adjacent absorbent arrays as a continuous sheet or array or (2) deposited, injected, or otherwise disposed in spaced locations. Depending upon the material disposed between absorbent arrays and whether it is continuous or discontinuous, adjacent absorbent arrays separated by such a material can be attached to each other or to the interposed material.

As shown in FIGS. 3–6, when the absorbent arrays 30 are oriented "vertically" to produce an absorbent core structure employed in an absorbent core of a disposable absorbent garment as described above, acquisition cells 40 are open the entire distance between the liner sheet 14 and the backing sheet 12, facilitating the rapid distribution of liquid away from the skin of the wearer of the absorbent garment. Optionally, holes or spaces can also be provided in the absorbent core structure, e.g., holes across one or more absorbent arrays to further facilitate fluid transfer throughout the absorbent core structure by mass flow. The absorbent core structure can also comprise one or more wicking layers 41 in liquid contact with an open end of the acquisition cells, e.g., disposed between the absorbent core structure 16 and the backing sheet 12, in order to assist in liquid transfer throughout the absorbent core structure. Such a wicking layer is preferably composed of a conventional hydrophilic woven sheet material.

Although the absorbent core structure has been described primarily with absorbent arrays oriented "vertically," it should be understood that absorbent core structures can also be produced wherein the absorbent arrays are layered substantially "horizontally," in which case the general plane of the absorbent array is parallel to the planes of the backing sheet 12 and liner sheet 14, as shown in FIGS. 9 and 10. Absorbent arrays consisting of multiple rows of storage cells, as described below, are particularly useful in producing an absorbent core having such a "horizontal" orientation. In an absorbent core having absorbent arrays in a horizontal orientation, the acquisition cells 40, are not open vertically, i.e., the entire distance between the liner sheet 14 and the backing sheet 12. If desired, holes or spaces may be introduced between in the absorbent arrays, for example, to allow fluids to move by mass flow vertically through the absorbent structure.

An alternate method of making an absorbent array for an absorbent core structure according to the present invention is shown in FIG. 7. Instead of employing two separate strips 31, 32 as shown in FIG. 2, a single double-width strip 42 of liquid-pervious material is folded lengthwise to produce facing halves 42a, 42b. Each of the facing halves 42a, 42b has an open longitudinal edge 43a, 43b, respectively. The two facing halves 42a, 42b share a longitudinal closed edge at the fold 44. Discrete quantities of superabsorbent material 34 are deposited at spaced locations between the facing halves 42a, 42b by a superabsorbent injector 45. The facing halves 42a, 42b are then attached together at spaced locations by sonic bonding to form bonds 50, 51 between the locations of the superabsorbent material 34 and along the open edge 43a, 43b of the folded sheet-like material, respectively, thereby producing storage cells 36. (Optionally, a bond 52 can also be formed along the fold 44.) The spacing and width of the bonds 50, 52 thus formed are defined by edges 50a, 51a (and, if there is a bond 52 along the fold 44, edge 52a) of a rotatable mandrel 46. The mandrel 46 is used to direct and focus ultrasonic energy produced by an ultrasonic transducer (not shown) onto a defined area of the facing halves 42a, 42b, causing them to be sonically bonded together to form bonds 50, 51 (and, if present, 52). (The mandrel 46 alone is shown in FIG. 8.) After sonic bonding, an adhesive applicator 54 applies a spot (or stripe or line) of adhesive 38 on an outer surface of the absorbent array 30, e.g., at an external location approximately central to, or in the mid-region of, each of the storage cells 36, as shown. The elongate absorbent array thus produced is finally cut to the desired length (not shown) and layered as described above to produce an absorbent core structure.

As an additional alternative, superabsorbent material can be disposed in preformed pockets in a liquid-pervious sheet. A second liquid-pervious sheet, e.g., a flat sheet, can then be attached to the second sheet, capturing the superabsorbent material in the pockets.

As a further alternative, superabsorbent material can be introduced into preformed cells produced, by the attachment of facing strips or sheets to each other. The cells containing the superabsorbent material are then sealed to produce discrete storage cells. Some preformed cells can remain free of superabsorbent material so as to serve as acquisition cells.

In the embodiment of the invention shown in FIGS. 2C and 2D, each absorbent array 30 has a single row, or linear array, of storage cells 36. FIG. 9 shows that each absorbent array 30 can alternatively have a two-dimensional pattern, e.g., multiple rows, of storage cells 36. In order to produce an absorbent array having such a two-dimensional pattern of storage cells, a method analogous to that shown in FIGS. 2A and 2B can be used, for example. Opposed strips 31, 32 are replaced by first and second sheets of a similar liquid-pervious material, each sheet preferably having the same shape and dimensions, e.g., a square, rectangular, hourglass, or other shape. Superabsorbent material 34 is deposited on the second sheet at spaced locations in a two-dimensional pattern, which can be either regular or irregular. The two sheets are bonded, sealed, or otherwise attached to each other by any conventional means to create bonds along each of their combined edges (not shown) and between each location of superabsorbent material 33e so as to define multiple fully-enclosed storage cells in each absorbent array, each cell having captured within it a quantity of superabsorbent material.

Absorbent arrays having a two-dimensional pattern of storage cells can be attached to each other, for example with glue spots or stripes positioned approximately central to, or in a mid-region of, all or selected storage cells, in order to produce a multi-layered absorbent core structure 16. FIG. 10 shows a cross-section of such an absorbent core structure in which the layers are in a "horizontal" orientation.

In absorbent core structure having a honeycomb-like configuration as shown, for example, in FIGS. 5 and 6, storage cells alternate with acquisition cells and the ratio of both the relative numbers of storage and acquisition cells and their cross-sectional areas is approximately 1:1. However, the ratio of the number or cross-sectional area of storage cells to acquisition cells in an absorbent core structure according to the invention can vary widely.

FIGS. 2–6 show an absorbent core structure in which the absorbent arrays are identical in configuration and have a parallel orientation with respect to each other. Nonetheless, there is intended to be no limitation regarding the configuration of the individual absorbent arrays in an absorbent core structure according to the invention or in the orientation of adjacent absorbent arrays with respect to each other. The storage and acquisition cells of a honeycomb-like absorbent core structure according to the invention can have a variety of regular or irregular shapes (including cubic, cylindrical, pyramidal, etc.), sizes, and configurations. Each absorbent array 30 can comprise a number of differently shaped storage cells, and different arrays of a multi-layer absorbent core can have similar or dissimilar patterns of storage cells. The shapes and sizes of the storage cells 36 can be varied, for example, by varying the configuration, spacing, and width of the bonds 33e by which facing strips of sheet material 32 in each layer 30 are attached to each other. Similarly, the size and shape of the acquisition cells 40 can be varied, for example, by varying (1) the manner in which adjacent absorbent arrays of the absorbent core structure are attached to each other (e.g., the spacing, location, width, and configuration of attachment sites); and (2) the orientation of each absorbent array in the structure with respect to adjacent absorbent arrays.

Absorbent core structures as described above can also be stacked or layered to form a thicker, more absorbent structure, e.g., with liquid-pervious sheets optionally separating adjacent layers.

Having illustrated and described the invention generally with respect to preferred embodiments, it should be apparent to those skilled in the art that modifications are possible without departing from the spirit of the invention.

What is claimed is:

1. An absorbent core structure comprising a plurality of absorbent arrays, each absorbent array comprising (a) facing liquid-pervious sheet portions and superabsorbent material disposed between the sheet portions, the facing sheet portions being attached to each other to define a plurality of discrete liquid-absorbent storage cells that contain the superabsorbent material, wherein each absorbent array is attached to another of the absorbent arrays, and (b) a plurality of acquisition cells between the absorbent arrays that are devoid of material that would impede liquid movement therethrough, wherein the acquisition cells expand upon liquid absorption by the storage cells.

2. The absorbent core structure of claim 1 wherein at least some of the acquisition cells are empty.

3. The absorbent core structure of claim 1 wherein the facing liquid-pervious sheet portions are facing half-sheets produced by folding a liquid-pervious sheet longitudinally to produce the half-sheets on opposite sides of a folded edge.

4. The absorbent core structure of claim 3 wherein each of the absorbent arrays comprises the folded edge, a longitudinal edge remote from the folded edge, and spaced first and second end edges and the half-sheets are attached to each other along the longitudinal edge and at the first and second end edges.

5. The absorbent core structure of claim 4 wherein a superabsorbent material is disposed between the facing half-sheets at spaced locations and the half-sheets are attached to each other between the locations of the superabsorbent material to define the discrete storage cells.

6. The absorbent core structure of claim 1 wherein the facing liquid-pervious sheet portions are facing first and second liquid-pervious sheets or strips.

7. The absorbent core structure of claim 6 wherein each of the sheets or strips comprises spaced first and second longitudinal edges and spaced first and second end edges and the first and second sheets or strips are attached to each other along the spaced first and second longitudinal edges and along the spaced first and second end edges.

8. The absorbent core structure of claim 7 wherein a superabsorbent material is disposed between the facing sheets or strips at spaced locations and the facing sheets or strips are attached to each other between the locations of the superabsorbent material, thereby defining the storage cells.

9. The absorbent core structure of claim 1 wherein each absorbent array comprises a linear array of the storage cells.

10. The absorbent core structure of claim 1 wherein each of the storage cells has a midregion and each absorbent array is attached to another of the absorbent arrays at approximately the midregions of a plurality of said storage cells.

11. The absorbent core structure of claim 1 wherein the storage cells alternate with the acquisition cells.

12. The absorbent core structure of claim 1 wherein the storage cells and the acquisition cells are arranged in a honeycomb-like configuration.

13. An absorbent core structure comprising a plurality of absorbent arrays and a plurality of acquisition cells that are devoid of material that would impede liquid movement through the acquisition cell, each of the absorbent arrays comprising facing liquid-pervious sheet portions and superabsorbent material disposed at spaced locations between the sheet portions, the opposed sheet portions being attached to each other between the locations of the superabsorbent material to define a plurality of discrete liquid-absorbent storage cells, each of the storage cells containing a superabsorbent material, wherein each of the absorbent arrays is attached to another of the absorbent arrays to define a plurality of the acquisition cells between the adjacent absorbent arrays and the storage cells, the acquisition cells expand upon liquid absorption by the storage cells, and the storage cells and acquisition cells are in a honeycomb-like configuration.

14. A disposable absorbent garment comprising:

a liquid-impervious backing sheet;

a liquid-pervious liner sheet; and an absorbent core between the backing and liner sheets, the absorbent core comprising (a) a plurality of absorbent arrays, each absorbent array comprising facing liquid-pervious sheet portions and superabsorbent material disposed between the sheet portions, the opposed sheet portions being attached to each other to define a plurality of discrete liquid-absorbent storage cells that contain the superabsorbent material, wherein each absorbent array is attached to another of the absorbent arrays, and (b) a plurality of acquisition cells between the absorbent arrays that are devoid of material that would impede liquid movement therethrough, wherein the acquisition cells expand upon liquid absorption by the storage cells.

15. The garment of claim 14 wherein the absorbent arrays are in a substantially perpendicular orientation relative to the backing and the liner sheets.

16. The garment of claim 14 wherein the absorbent arrays are in a substantially parallel orientation relative to the backing and the liner sheets.

17. The garment of claim 14 wherein at least some of the acquisition cells are empty.

18. The garment according to claim 14 further comprising a wicking layer in fluid contact with the absorbent core.

* * * * *